(12) United States Patent
Tuttle

(10) Patent No.: US 9,498,010 B2
(45) Date of Patent: Nov. 22, 2016

(54) APPARATUS FOR PROVIDING WATERTIGHT PROTECTION TO AN APPENDAGE

(76) Inventor: Theresa M. Tuttle, Wappingers Falls, NY (US)

( * ) Notice: Subject to any disclaimer, the term of this patent is extended or adjusted under 35 U.S.C. 154(b) by 857 days.

(21) Appl. No.: 13/398,387

(22) Filed: Feb. 16, 2012

(65) Prior Publication Data

US 2013/0212774 A1    Aug. 22, 2013

(51) Int. Cl.
| | |
|---|---|
| A41D 13/06 | (2006.01) |
| A41D 19/015 | (2006.01) |
| A43B 23/07 | (2006.01) |
| A41D 13/05 | (2006.01) |
| A41D 13/08 | (2006.01) |
| A61F 15/00 | (2006.01) |

(52) U.S. Cl.
CPC ......... *A41D 19/015* (2013.01); *A41D 13/0556* (2013.01); *A41D 13/06* (2013.01); *A41D 13/08* (2013.01); *A43B 23/07* (2013.01); *A61F 15/004* (2013.01)

(58) Field of Classification Search
CPC .......................... A41D 19/0055; A61F 15/004
USPC ....................................... 2/161.7, 162; 602/3
See application file for complete search history.

(56) References Cited

U.S. PATENT DOCUMENTS

| | | | |
|---|---|---|---|
| 2,030,135 A * | 2/1936 | Carpenter ..................... | 24/67 R |
| 2,911,974 A * | 11/1959 | Spence ......................... | 604/312 |
| 4,523,586 A * | 6/1985 | Couri ............................. | 602/3 |
| 4,727,864 A * | 3/1988 | Wiesenthal et al. .............. | 602/3 |
| 4,845,780 A | 7/1989 | Reimers et al. | |
| 4,884,300 A * | 12/1989 | Vistins .............................. | 2/162 |
| 5,016,648 A * | 5/1991 | Brown et al. .................. | 128/846 |
| 5,035,687 A | 7/1991 | Sandbank | |
| 5,152,282 A * | 10/1992 | Elphick et al. ............... | 604/180 |
| 5,342,286 A * | 8/1994 | Kelly et al. ......................... | 602/3 |
| 5,630,430 A | 5/1997 | Shultz et al. | |
| 5,643,183 A * | 7/1997 | Hill ..................................... | 602/3 |
| 5,867,832 A * | 2/1999 | Liu ................................ | 2/161.7 |
| 6,442,761 B1 | 9/2002 | Huang | |
| 6,512,158 B1 * | 1/2003 | Dobos ............................ | 602/41 |
| 2006/0185059 A1 | 8/2006 | Taha | |
| 2010/0017939 A1 | 1/2010 | Carpenter, Jr. | |

FOREIGN PATENT DOCUMENTS

EP            695157 B1        3/1998

* cited by examiner

*Primary Examiner* — Richale Quinn
(74) *Attorney, Agent, or Firm* — Law Offices of Michael L. Wise, LLC

(57) ABSTRACT

An apparatus comprises an upper portion and a lower portion. The upper portion defines an upper edge region, while the lower portion defines a lower edge region. An upper adhesive band is disposed on the upper portion and runs alongside substantially the entire upper edge region. An upper release liner, in turn, is disposed on at least a portion of the upper adhesive band. At the same time, a lower adhesive band is disposed on the lower portion and runs alongside substantially the entire lower edge region. A lower release liner is disposed on at least a portion of the lower adhesive band. The lower portion is joined to the upper portion so as to define a hollow enclosure therebetween with the upper edge region and the lower edge region forming an open end in the hollow enclosure. The upper adhesive band and the lower adhesive band are disposed inside the hollow enclosure.

9 Claims, 5 Drawing Sheets

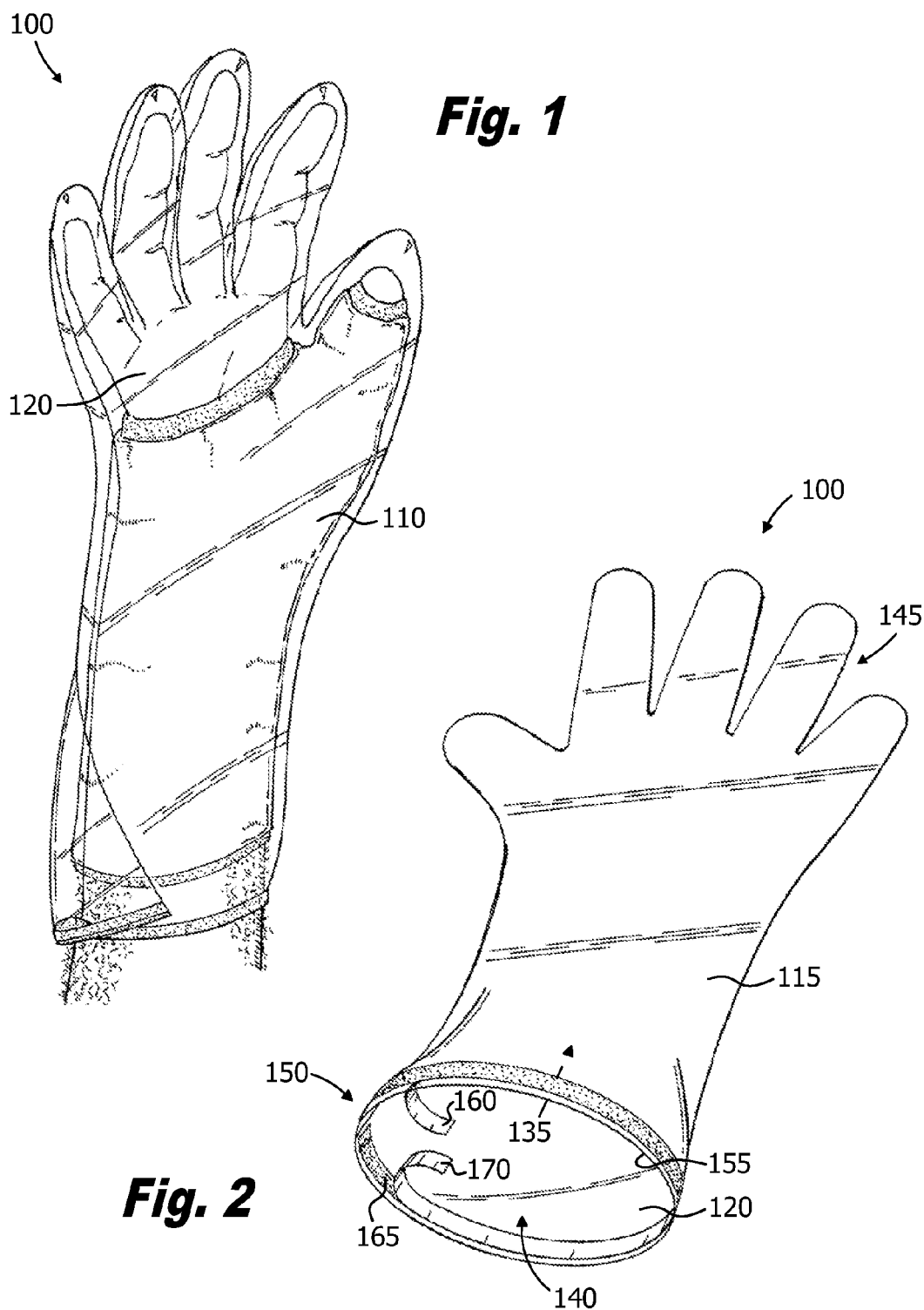

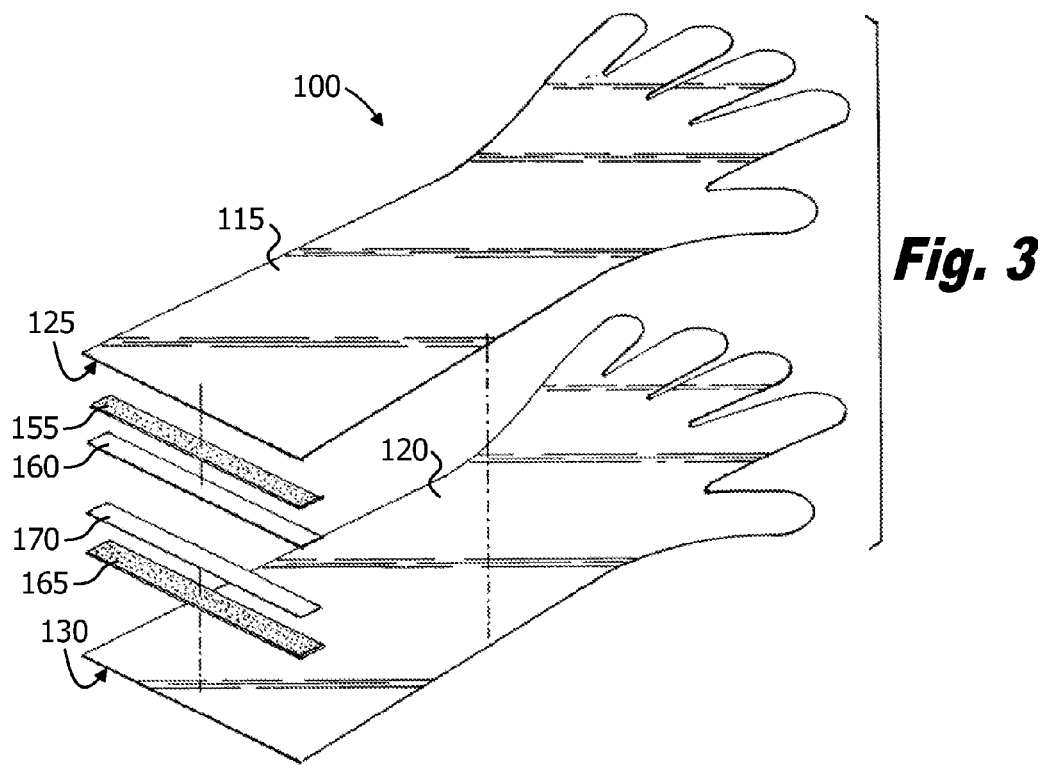
*Fig. 3*
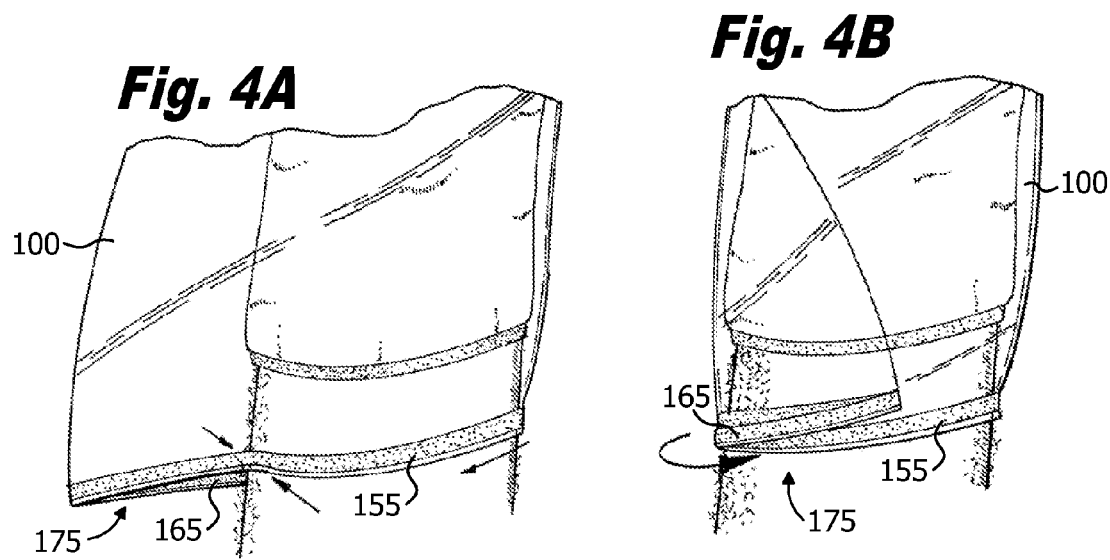
*Fig. 4A*
*Fig. 4B*

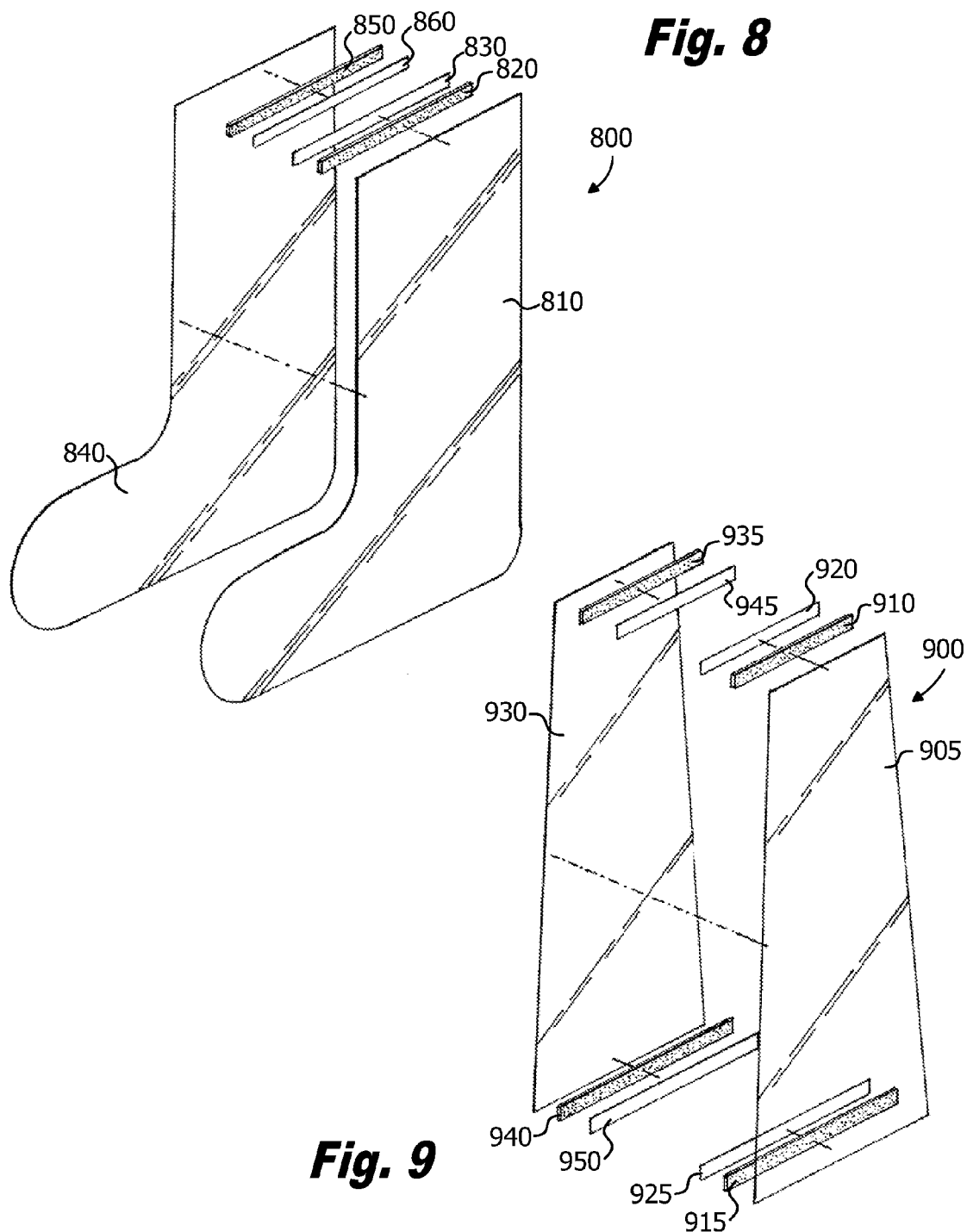

APPARATUS FOR PROVIDING WATERTIGHT PROTECTION TO AN APPENDAGE

FIELD OF THE INVENTION

The present invention relates generally to apparatus and methods for providing watertight protection to an appendage, and, more particularly, to gloves, boots, and sleeves adapted to provide watertight protection to an arm, hand, leg, or foot.

BACKGROUND OF THE INVENTION

There are many situations that demand that a person protect his or her arms, hands, legs, or feet from coming into contact with a liquid. A doctor, a nurse, or a lab technician may, for example, need to handle a bio-hazardous material. Likewise, a patient with a bandage, plaster cast, or intravenous catheter may desire to shower or bathe without having the bandage, cast, or catheter get wet.

As a result, there have been several attempts to produce gloves and boots that can provide a watertight covering for a person's extremities. These attempts include, for example, U.S. Pat. Nos. 4,727,864; 4,845,780; 4,884,300; 5,867,832; and 6,442,761; as well as U.S. Pat. Publication Nos. 2006/0185059 and 2010/0017939; and European Patent No. 695157. Each of these various designs relies on a mechanism for tightly closing the open end of the glove or boot around the wearer's appendage in order to produce a watertight seal. Nevertheless, these existing solutions suffer from several disadvantages. They are difficult to use, are ineffective at keeping the wearer dry, and/or are overly complex and therefore expensive to manufacture.

For the foregoing reasons, there is a need for a covering that is capable of providing reliable watertight protection to the wearer while, at the same time, remaining easy to use and inexpensive to manufacture.

SUMMARY OF THE INVENTION

Embodiments of the present invention address the above-identified needs by providing apparatus capable of offering reliable watertight protection to a wearer's arms, legs, hands, feet, or combinations thereof.

In accordance with aspects of the invention, such an apparatus comprises an upper portion and a lower portion. The upper portion defines an upper edge region, while the lower portion defines a lower edge region. An upper adhesive band is disposed on the upper portion and runs alongside substantially the entire upper edge region. An upper release liner, in turn, is disposed on at least a portion of the upper adhesive band. At the same time, a lower adhesive band is disposed on the lower portion and runs alongside substantially the entire lower edge region. A lower release liner is disposed on at least a portion of the lower adhesive band. The lower portion is joined to the upper portion so as to define a hollow enclosure therebetween with the upper edge region and the lower edge region forming an open end in the hollow enclosure. The upper adhesive band and the lower adhesive band are disposed inside the hollow enclosure.

Advantageously, aspects of the invention can easily be expanded from protective gloves to other form factors including, but not limited to, protective boots as well as protective sleeves. In each case, the apparatus, whatever its particular form, provides reliable protection against liquids, is easy to use, and is inexpensive to manufacture.

BRIEF DESCRIPTION OF THE DRAWINGS

These and other features, aspects, and advantages of the present invention will become better understood with regard to the following description, appended claims, and accompanying drawings where:

FIG. 1 shows a perspective view of a glove in accordance with an illustrative embodiment of the invention while in use to protect an injured hand;

FIG. 2 shows another perspective view of the FIG. 1 glove;

FIG. 3 shows an exploded perspective view of the FIG. 1 glove;

FIGS. 4A and 4B show perspective views of the open end portion of the FIG. 1 glove while in use;

FIG. 8 shows an exploded perspective view of a boot in accordance with an illustrative embodiment of the invention; and FIG. 9 shows an exploded perspective view of a sleeve in accordance with an illustrative embodiment of the invention.

DETAILED DESCRIPTION OF THE INVENTION

Figure 5:
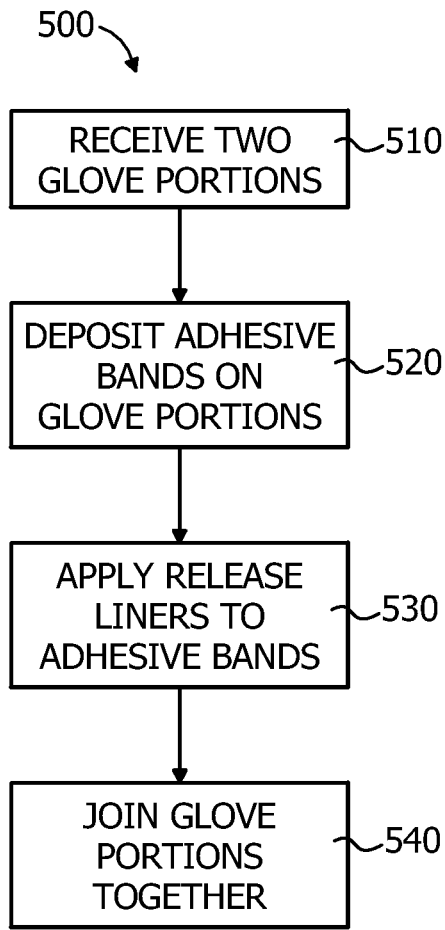
FIG. 5 shows a flowchart of a first illustrative method for forming the FIG. 1 glove.

The present invention will be described with reference to illustrative embodiments. For this reason, numerous modifications can be made to these embodiments and the results will still come within the scope of the invention. No limitations with respect to the specific embodiments described herein are intended or should be inferred.

FIGS. 1-3 show several views of a predominantly transparent glove 100 in accordance with an illustrative embodiment of the invention. More particularly, FIG. 1 shows a perspective view of the glove 100 while in use to protect an injured hand; FIG. 2 shows a perspective view of the glove 100 before being used; and FIG. 3 shows an exploded perspective view the glove 100.

As shown in FIG. 1, one possible use of the illustrative glove 100 is to protect a cast 105 on a wearer's forearm 110 from coming into contact with water while, for example, the wearer showers or bathes. Nevertheless, this is only one such possible use of embodiments of the invention. Other uses include, but are not limited to, preventing a wearer's bandage or intravenous catheter from getting wet, as well as protecting a doctor, a nurse, or a lab technician from coming into direct contact with bio-hazardous material.

Now referring to FIGS. 2 and 3, the illustrative glove 100 comprises two portions: an upper glove portion 115 and a lower glove portion 120, both of which are substantially transparent to visible light. The upper glove portion 115 defines an upper edge region 125, while the lower glove portion 120 defines a lower edge region 130. When these two portions are aligned and joined together as shown in FIG. 3, the upper glove portion 115 and the lower glove portion 120 define a hollow enclosure 135 therebetween. At the same time, the upper edge region 125 and the lower edge region 130 form an open end 140 in the hollow enclosure 135. The open end 140 is sized such that a wearer may insert that wearer's hand and forearm into the hollow enclosure 135. Opposite the open end 140, the hollow enclosure 135 terminates in a finger portion 145 adapted to enclose the wearer's thumb and fingers. Before it is used, the glove 100 is laid substantially flat in the manner in which many disposable gloves are packaged and presented to the end-user.

In accordance with aspects of the invention, a novel closure mechanism 150 is located proximate to the open end 140 of the glove 100. The closure mechanism 150 provides a means for allowing the wearer to seal the open end 140 of the glove 100 about the wearer's forearm. In so doing, the closure mechanism 150 prevents liquids from entering the glove 100, thereby providing watertight protection to the wearer.

Still referring to FIGS. 2 and 3, it will be observed that the closure mechanism 150 comprises several elements, namely, an upper adhesive band 155, an upper release liner 160, a lower adhesive band 165, and a lower release liner 170. As can be seen in the figures, the upper adhesive band 155 is disposed on the upper glove portion 115 and runs alongside substantially the entire upper edge region 125. The upper release liner 160, in turn, is disposed on the upper adhesive band 155. In a similar manner, the lower adhesive band 165 is disposed on the lower glove portion 120 and runs alongside substantially the entire lower edge region 130. The lower release liner 170 is disposed on the lower adhesive band 165. When the glove 100 is formed, each of the upper adhesive band 155 and the lower adhesive band 165 end up inside the hollow enclosure 135, facing each other on opposing glove portions 115, 120 of the glove 100.

Once the closure mechanism 150 is so configured, forming a sealed, watertight closure around the wearer's forearm becomes relatively easy. The wearer inserts the wearer's hand and forearm into the glove 100 and then the wearer, or alternatively a person helping the wearer, pulls the upper release liner 160 and the lower release liner 170 away from the glove 100. Removing the release liners 160, 170 exposes the upper adhesive band 155 and the lower adhesive band 165. Exposed in this manner, portions of the adhesive bands 155, 165 are made to directly contact the wearer's skin and to form a seal thereto. Those portions of the upper adhesive band 155 and the lower adhesive band 165 that do not fall on the wearer's skin are instead pressed against each other to form one or more flaps that take up this excess cuff area.

FIGS. 4A and 4B show perspective views of the open end portion of the glove 100 while sealed about a wearer's forearm. In this example, the upper adhesive band 155 is directly sealed to the lower adhesive band 165 to form a flap 175 that is located laterally to the wearer's forearm. In this manner, the closure mechanism 150 forms a watertight seal even in those areas where the adhesive bands 155, 165 are not adhered directly to the wearer's skin. Optionally, if it is desired that the flap 175 not protrude laterally in the manner shown in FIG. 4A, the flap 175 may be further folded over onto the remainder of the glove 100, as shown in FIG. 4B. Slightly misaligning the opposed parts of the adhesive bands 155, 165 that form the flap 175 has been found to be an effective way of exposing just enough adhesive to adhere the flap 175 against the remainder of the glove 100 in this manner. Because of the ability of the closure mechanism 150 to accommodate excess cuff area, the glove 100 may be substantially oversized in relation to the wearer, thereby facilitating "one size fits all" and not requiring that several different sizes be made available. Gloves configured as shown in both FIGS. 4A and 4B have been determined to provide excellent watertight protection to a wearer.

It is noted that the upper adhesive band 155 and the lower adhesive band 165 in the glove 100 are located substantially adjacent to the upper edge region 125 and to the lower edge region 130, respectively. Such a configuration is preferable, although not required. Spaces between the adhesive bands 155, 165 and the edge regions 125, 130 are places where liquids may get trapped while the glove 100 is in use. Trapped liquids may, in turn, further test the closure mechanism 150 and potentially act as sources of leaks. Accordingly, it is desirable to avoid such spaces where possible.

The glove portions 115, 120 of the glove 100 may comprise polyethylene or any other equally suitable material (clear or opaque) such as vinyl, natural rubber latex, synthetic latex, and the like, all of which are readily available from commercial sources. Suitable adhesives for the adhesive bands 155, 165 are also commercially available. One particularly suitable adhesive is that used by 3M (St. Paul, Minn., USA) in their Double Coated Medical Tape, Product Number 1509. This adhesive comprises an acrylate and has been proven to be well suited for medical and surgical applications wherein it comes directly in contact with human skin. Such an adhesive may be applied by, for example, spraying, brushing, rolling, and the like. Finally, the release liners 160, 170 may comprise any suitable release liner material that is able to readily release the adhesive bands 155, 165 such as, but not limited to, kraft paper, glassine paper, clay-coated paper, polyethylene-protected paper, polyester, polypropylene, and combinations thereof.

Manufacture of the glove 100 may be accomplished in several ways, the automation of which will be well within the capabilities of one having ordinary skills in the automation arts. A first illustrative method 500 is described in the flowchart shown in FIG. 5. In a step 510, the upper glove portion 115 and the lower glove portion 120 are received. Next, in a step 520, the upper adhesive band 155 and the lower adhesive band 165 are deposited on the upper glove portion 115 and the lower glove portion 120, respectively, such that the upper adhesive band 155 runs alongside substantially the entire upper edge region 125 and the lower adhesive band 165 runs alongside substantially the entire lower edge region 130. In a step 530, the upper release liner 160 and the lower release liner 170 are applied to the upper adhesive band 155 and the lower adhesive band 165, respectively. Lastly, in a step 540, the upper glove portion 115 is joined to the lower glove portion 120 to form the glove 100. When joined, the lower glove portion 120 and the upper glove portion 115 define the hollow enclosure 135 with the upper edge region 125 and the lower edge region 130 forming the open end 140.

Joining the upper glove portion 115 to the lower glove portion 120 may be performed by several conventional joining techniques including, but not limited, to heat sealing (also called plastic welding). Heat-sealed, polyethylene gloves are commonly used in, for example, the food industry. A heat sealer is a machine used to seal products, packaging, and other thermoplastic materials using heat. Heat sealing is described in several readily available publications including, for example, K. Hishinuma, *Heat Sealing Technology and Engineering for Packaging: Principles and Applications*, DEStech Publications, Inc., 2009, which is hereby incorporated by reference herein.

Figure 6:
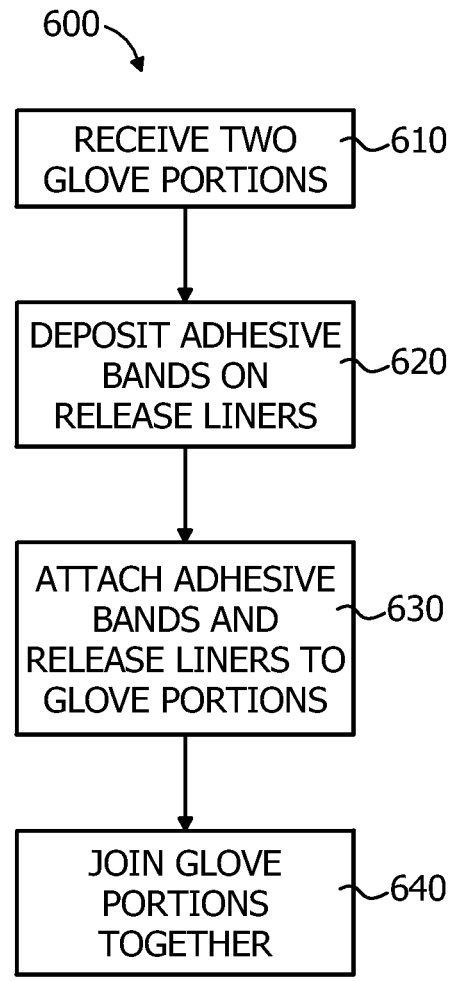
FIG. 6 shows a flowchart of a second illustrative method for forming the FIG. 1 glove.

A second alternative illustrative method 600 is described in the flowchart in FIG. 6. Here, the adhesive bands 155, 165 are applied to the release liners 160, 170 first, and these combined entities are then applied to the glove portions 115, 120. More particularly, in a step 610, the upper glove portion 115 and the lower glove portion 120 are received. Next, in a step 620, the upper adhesive band 155 and the lower adhesive band 165 are deposited on the upper release liner 160 and the lower release liner 170, respectively. Then, in a step 630, the upper adhesive band 155 and the upper release liner 160 are attached to the upper glove portion 115, while the lower adhesive band 165 and the lower release liner 170 are attached to the lower glove portion 120. Lastly, in a step 540, the upper glove portion 115 is joined to the lower glove portion 120 to again form the glove 100.

Figure 7:
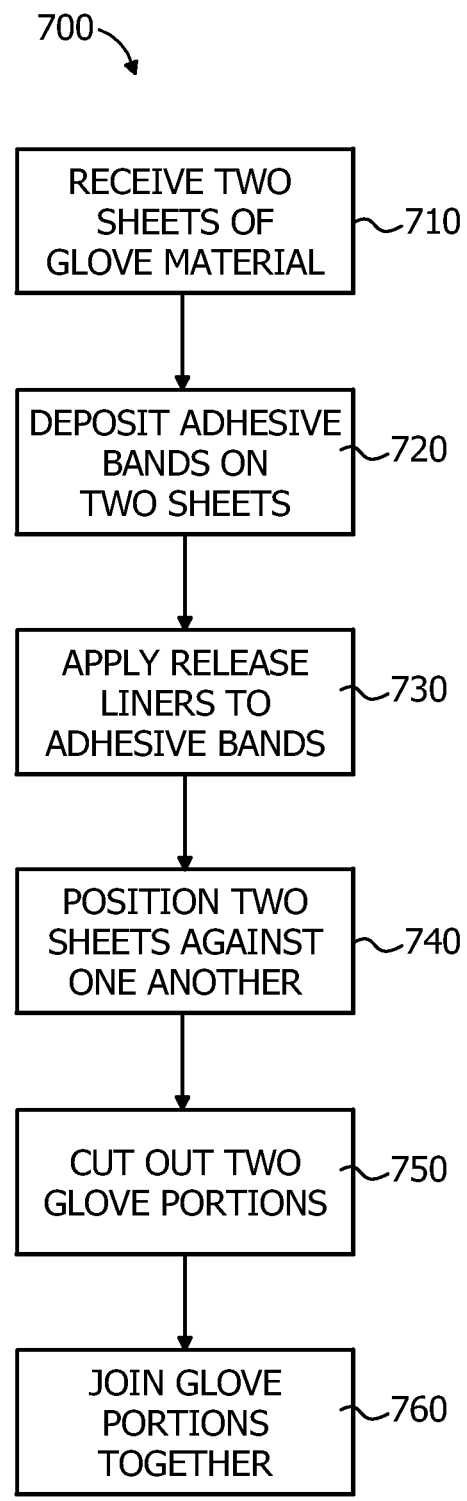
FIG. 7 shows a flowchart of a third illustrative method for forming the FIG. 1 glove.

Even a third alternative illustrative method 700 for forming the glove 100 is described in the flowchart in FIG. 7. In the method 700, the glove 100 is formed by starting with two sheets of the material that will ultimately form the upper glove portion 115 and the lower glove portion 120 (e.g., two sheets of polyethylene) but are yet undefined. These two sheets are received in a step 710. In a step 720, the upper adhesive band 155 and the lower adhesive band 165 are deposited on respective ones of these two sheets. Next, in a step 730, the upper release liner 160 and the lower release liner 170 are applied to the upper adhesive band 155 and the lower adhesive band 165, respectively. In a step 740, the two sheets are positioned such that the upper release liner 160 overlies substantially all of the lower release liner 170. With the adhesive bands 155, 165 and release liners 160, 170 lined up in this manner, the two sheets are then simultaneously cut so as to form the upper glove portion 115 and the lower glove portion 120, as indicated in a step 750. The cutting is performed such that the upper adhesive band 155 runs alongside substantially the entire upper edge region 125 of the upper glove portion 115, and the lower adhesive band 165 runs alongside substantially the entire lower edge region 130 of the lower glove portion 120. Finally, in a step 760, the upper glove portion 115 is joined to the lower glove portion 120 to again form the glove 100.

Notably, while the illustrative glove embodiment described above is designed to protect a wearer's forearm and hand from contact with liquids, the invention is not limited to this particular application. Instead, aspects of the invention may be applied to providing watertight protection to several different appendages (or portions thereof). FIG. 8, for example, shows a boot 800 in accordance with an illustrative embodiment of the invention for protecting a wearer's leg and foot. The boot 800 comprises an upper boot portion 810, an upper adhesive band 820, an upper release liner 830, a lower boot portion 840, a lower adhesive band 850, and a lower release liner 860. When combined, these elements form a boot with a closure mechanism similar to the closure mechanism 150 in the glove 100. FIG. 9, in turn, shows a sleeve 900 in accordance with another illustrative embodiment of the invention. The sleeve 900 comprises an upper sleeve portion 905, two upper adhesive bands 910, 915, two upper release liners 920, 925, a lower sleeve portion 930, two lower adhesive bands 935, 940, and two lower release liners 945, 950. In so doing, when joined, the sleeve 900 forms a hollow enclosure defining two open ends with respective closure mechanisms similar to the closure mechanism 150. The sleeve 900 is therefore suitable for protection of a portion of the wearer's arm or leg, while, at the same time, leaving the wearer's corresponding hand or foot uncovered.

It should again be emphasized that the above-described embodiments of the invention are intended to be illustrative only. Other embodiments can use different types and arrangements of elements, or different method steps, for implementing the described functionality. These numerous alternative embodiments within the scope of the appended claims will be apparent to one skilled in the art.

Moreover, all the features disclosed herein may be replaced by alternative features serving the same, equivalent, or similar purposes, unless expressly stated otherwise. Thus, unless expressly stated otherwise, each feature disclosed is one example only of a generic series of equivalent or similar features.

What is claimed is:

1. A method of forming an apparatus for providing watertight protection to an appendage, the method comprising the steps of:
    (a) receiving an upper portion defining an upper edge region;
    (b) after step (a), disposing an upper adhesive band on the upper portion such that the upper adhesive band runs alongside substantially the entire upper edge region;
    (c) after step (b), disposing an upper release liner on at least a portion of the upper adhesive band;
    (d) receiving a lower portion defining a lower edge region and separate from the upper portion;
    (e) after step (d), disposing a lower adhesive band on the lower portion such that the lower adhesive band runs alongside substantially the entire lower edge region;
    (f) after step (e), disposing a lower release liner on at least a portion of the lower adhesive band; and
    (g) after steps (a) through (f), joining part of an outside edge of the lower portion to part of an outside edge of the upper portion so as to define a hollow enclosure therebetween with the upper edge region and the lower edge region forming an open end in the hollow enclosure and with the upper adhesive band and the lower adhesive band disposed inside the hollow enclosure.

2. The method of claim 1, wherein the apparatus forms at least part of a glove.

3. The method of claim 1, wherein the apparatus forms at least part of a boot.

4. The method of claim 1, wherein the hollow enclosure defines a second open end.

5. A method of forming an apparatus for providing watertight protection to an appendage, the method comprising the steps of:
    (a) receiving an upper portion defining an upper edge region;
    (b) disposing an upper adhesive band on an upper release liner;
    (c) after steps (a) and (b), disposing the upper adhesive band and the upper release liner on the upper portion such that the upper adhesive band runs alongside substantially the entire upper edge region;
    (d) receiving a lower portion defining a lower edge region and separate from the upper portion;
    (e) disposing a lower adhesive band on a lower release liner;
    (f) after steps (d) and (e), disposing the lower adhesive band and the lower release liner on the lower portion such that the lower adhesive band runs alongside substantially the entire lower edge region; and
    (g) after steps (a) through (f), joining part of an outside edge of the lower portion to part of an outside edge of the upper portion so as to define a hollow enclosure therebetween with the upper edge region and the lower edge region forming an open end in the hollow enclosure and with the upper adhesive band and the lower adhesive band disposed inside the hollow enclosure.

6. A method of forming an apparatus for providing watertight protection to an appendage, the method comprising the steps of:
    (a) receiving an upper sheet;

(b) after step (a), disposing an upper adhesive band on the upper sheet;

(c) after step (b), disposing an upper release liner on at least a portion of the upper adhesive band;

(d) receiving a lower sheet separate from the upper sheet;

(e) after step (d), disposing a lower adhesive band on the lower sheet;

(f) after step (e), disposing a lower release liner on at least a portion of the lower adhesive band;

(g) after step (c), cutting the upper sheet to define an upper portion with an upper edge region, the upper adhesive band running alongside substantially the entire upper edge region;

(h) after step (f), cutting the lower sheet to define a lower portion with a lower edge region, the lower adhesive band running alongside substantially the entire lower edge region; and (i) after steps (a) through (h), joining part of an outside edge of the lower portion to part of an outside edge of the upper portion so as to define a hollow enclosure therebetween with the upper edge region and the lower edge region forming an open end in the hollow enclosure and with the upper adhesive band and the lower adhesive band disposed inside the hollow enclosure.

7. The method of claim 6, wherein the apparatus forms at least part of a glove.

8. The method of claim 6, wherein the apparatus forms at least part of a boot.

9. The method of claim 6, wherein the hollow enclosure defines a second open end.

\* \* \* \* \*